US010580277B2

(12) United States Patent
Penney et al.

(10) Patent No.: US 10,580,277 B2
(45) Date of Patent: Mar. 3, 2020

(54) CHAMBERLESS SMOKE DETECTOR

(71) Applicant: Tyco Fire & Security GmbH, Neuhausen am Rheinfall (CH)

(72) Inventors: Stephen J. Penney, Middlesex (GB); Andrew Naish, Surrey (GB); Steven Bennett, Middlesex (GB); Faruk Meah, Surrey (GB)

(73) Assignee: Johnson Controls Fire Protection LP, Boca Raton, FL (US)

( * ) Notice: Subject to any disclaimer, the term of this patent is extended or adjusted under 35 U.S.C. 154(b) by 0 days.

(21) Appl. No.: 16/123,724

(22) Filed: Sep. 6, 2018

(65) Prior Publication Data

US 2019/0080579 A1    Mar. 14, 2019

(30) Foreign Application Priority Data

Sep. 8, 2017 (EP) .................................... 17190223

(51) Int. Cl.
*G08B 17/107* (2006.01)
*G08B 17/113* (2006.01)
*G01N 21/53* (2006.01)

(52) U.S. Cl.
CPC .......... *G08B 17/107* (2013.01); *G08B 17/113* (2013.01); *G01N 21/532* (2013.01)

(58) Field of Classification Search
CPC ... G01N 21/532; G08B 17/107; G08B 17/113
See application file for complete search history.

(56) References Cited

U.S. PATENT DOCUMENTS

| 7,151,460 | B2 | 12/2006 | Makela et al. | |
|---|---|---|---|---|
| 9,482,607 | B2 | 11/2016 | Erdtmann | |
| 2002/0080040 | A1 | 6/2002 | Schneider et al. | |
| 2006/0164241 | A1* | 7/2006 | Makela | G08B 17/107 340/556 |
| 2013/0176131 | A1* | 7/2013 | Pichard | G01N 21/53 340/630 |
| 2015/0204781 | A1* | 7/2015 | Wagner | G08B 17/107 356/342 |
| 2015/0346086 | A1* | 12/2015 | Erdtmann | G08B 17/107 250/574 |
| 2018/0061215 | A1* | 3/2018 | Vollenweider | G08B 29/043 |
| 2019/0180590 | A1* | 6/2019 | Fischer | G08B 17/107 |

OTHER PUBLICATIONS

Extended European Search Reort, dated Mar. 14, 2018, from European Patent Application No. 17190223.2 Filed Sep. 8, 2017. 7 pages.

* cited by examiner

*Primary Examiner* — Nader Bolourchi
(74) *Attorney, Agent, or Firm* — HoustonHogle LLP

(57) ABSTRACT

The detector has a first optical smoke detector having a first smoke detector light source arranged for emitting a first beam of light and a first scattered light sensor positioned to detect light from the first beam which is scattered by smoke present within a detection zone; a second optical smoke detector having a second smoke detector light source arranged for emitting a second beam of light and a second scattered light sensor positioned to detect light from the second beam which is scattered by smoke present within the detection zone; and an object proximity detector to detect an object in the detection zone.

12 Claims, 1 Drawing Sheet

CHAMBERLESS SMOKE DETECTOR

RELATED APPLICATIONS

This application claims priority to European Application Number: 17190223.2, filed on Sep. 8, 2017, which is incorporated herein by this reference in its entirety.

FIELD OF THE INVENTION

The present invention relates to chamberless smoke detectors, and more particularly to such detectors arranged to minimise the raising of false alarms.

BACKGROUND OF THE INVENTION

Most smoke detectors include a body which defines a chamber with openings to the surrounding air within which any airborne smoke particles can be detected. The chamber forms a controlled environment for detection. The chamber can be arranged such that it is insulated from entry of ambient light, and that the openings prevent ingress of insects and larger dirt particles. So long as the openings are kept clear of dirt, such smoke detectors have proven to be extremely reliable and to require limited maintenance.

Chamberless smoke detectors are a recent development, and as their name suggests, they are designed to detect smoke without using a chamber in the air outside of the body of the detector. Chamberless smoke detectors have the aesthetic advantage of having a lower profile because they do not require the body to include a chamber. Chamberless smoke detectors include a faceplate and smoke particles are detected in a detection region in front of the faceplate. One of the challenges in designing a chamberless smoke detector is that the detection region is not a controlled environment, and objects and light can enter the detection region without hindrance, which can result in the raising of false alarms too frequently. For example, an insect could enter the detection zone and cause a false alarm to be triggered. Alternatively, an object carried by a person might inadvertently be moved through the detection zone and cause a false alarm to be triggered. It is necessary to ensure that false alarms are minimised in order to save unnecessary disruption from unnecessary evacuations and to minimise call-outs from fire services and maintenance technicians.

A known chamberless smoke detector is the Bosch FCP-500. That detector seeks to minimise false alarms by having two smoke detectors mounted on the body which have completely separate detection regions so that, if an insect or object passes in front of the detector, it will only be detected by one detector at a time.

SUMMARY OF THE INVENTION

However, there are problems with these known approaches. Firstly, if the object is very large, it might span the gap between the two detection regions, causing the detector to determine that, since something has been detected by both smoke detectors, smoke must be present in the air, generating a false alarm. Secondly, the faceplate of the detector is very large in order to accommodate two separate detection regions. Thirdly, the detector is expensive to manufacture because it requires two identical detectors which are detecting what a single detector is capable of detecting.

The present invention seeks to minimise the likelihood of a false alarm being generated, and to reduce some of the other problems associated with the known detector.

According to a first aspect of the present invention, a chamberless smoke detector, comprises: a first optical smoke detector having a first smoke detector light source arranged for emitting a first beam of light and a first scattered light sensor positioned to detect light from the first beam which is scattered by smoke present within a detection zone; a second optical smoke detector having a second smoke detector light source arranged for emitting a second beam of light and a second scattered light sensor positioned to detect light from the second beam which is scattered by smoke present within the detection zone; and an object proximity detector to detect an object in the detection zone, wherein the first smoke detector light source and the first scattered light sensor are inclined, with respect to a line normal to the smoke detector, by a greater angle than the second smoke detector light source and the second scattered light sensor.

The proximity detector might comprise a proximity signal source arranged for emitting a proximity signal beam towards the detection zone and a reflected proximity signal sensor arranged with the proximity signal source to detect the signal reflected from an object. Preferably, the proximity signal source is an ultrasonic signal source, and the proximity signal sensor is an ultrasonic signal sensor. The use of an ultrasonic signal is advantageous because it tends to be reflected well by solid objects Having the first smoke detector light source and the first scattered light detector inclined to the normal by a greater angle than the second smoke detector light source and the second scattered light sensor permits good discrimination between different particulates, reducing the likelihood of an alarm condition being triggered by non-smoke particles, such as steam or dust.

It is also preferred that the first and second light sources are arranged to emit light of different frequencies. This permits good discrimination between different particulates, reducing the likelihood of an alarm condition being triggered by non-smoke particles, such as steam or dust.

In one arrangement, the first light source, the first light sensor and the proximity sensor are arranged in a straight line across the detector. This facilitates the use of a common detection zone, or, at least, a detection zone which has common regions of detection within it.

In another arrangement, the first light source, the first light sensor, the second light source, the second light sensor and the proximity sensor are arranged in a straight line across the detector. This facilitates the use of a common detection zone, or, at least, a detection zone which has common regions of detection within it.

In the present application, references to the fire detector being chamberless are to a detector being arranged to detect smoke outside of the body of the fire detector, and not within a chamber.

In the present application, reference is made to an object. The object is something which might be detected by a smoke detector. It might include an insect, an airborne ball, hanging Christmas decorations, or furniture being carried by a person, but it does not include small particles such as smoke particles, steam and dust.

In the present application, a proximity detector is a detector which detects the presence of an object.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

An embodiment of this invention will now be described by way of example only, and with reference to the attached drawings in which.

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Figure 1:
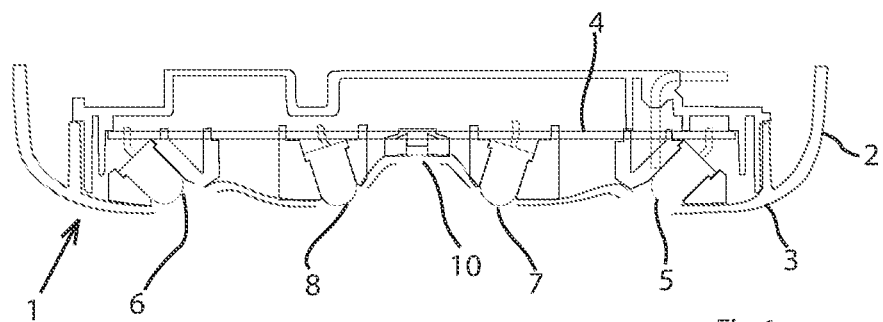
FIG. 1 is a schematic view of a chamberless smoke detector according to the present invention.

A chamberless smoke detector 1 is shown in FIG. 1, and includes a body 2 which extends across the front of the detector to form a faceplate 3. Within the body 2 is mounted a board 4 on which a number of electronic components are mounted. Those components include a first light source 5 and a first light sensor 6, the first light source 5 and the first light sensor 6 forming a first optical smoke detection system. The first light source 5 and the first light sensor 6 are disposed remotely from each other and are inclined obliquely away from the normal towards each other.

The components also include a second light source 7 and a second light sensor 8, the second light source 7 and the second light sensor 8 forming a second optical smoke detection system. The second light source 7 and the second light sensor 8 are disposed remotely from each other and are inclined obliquely away from the normal towards each other.

The distance between the second light source 7 and the second light sensor 8 is smaller than the distance between the first light source 5 and the first light sensor 6. Here, the light sources and the light sensors are arranged in a line across the body 2. Furthermore, the angle of inclination of the first light source 5 and the first light sensor 6 is greater than the angle of inclination of the second light source 7 and the second light sensor 8. However, they all point towards a common volume of space in front of the detector 1 which is the detection zone 9.

The components on the board also include a proximity detector 10 which is disposed centrally between the second light source 7 and the second light sensor 8. The proximity detector 10 is arranged to detect objects in front of the detector 1, and is arranged to be angled normally with respect to the detector 1. In other words, it is arranged to be perpendicular with respect to the body 2 of the detector 1. Furthermore, the proximity detector 10 is arranged to point towards the common detection zone 9.

The faceplate 3 includes a plurality of holes, and both of the light sources, both of the light sensors, and the proximity detector are in alignment with those holes in the faceplate 3 so that they are exposed. The components may project through the holes in the faceplate 3, or may simply be located behind the holes in the faceplate 3.

The first optical smoke detection system is designed to operate using a different wavelength of light to the second optical smoke detection system. In this embodiment, the first light source 5 emits light at a wavelength of about 450 nm, and the second light source 7 emits light at a wavelength of 880 nm. The first light sensor 6 is arranged to be able to detect the wavelength of light emitted by the first light source 5, and the second light sensor 8 is arranged to be able to detect the wavelength of light emitted by the second light source 7. The light sensors 6, 8 are further arranged such that they are not able to detect, to any substantial degree, light emitted by the light source of the other of the optical smoke detection systems. This allows the two optical smoke detection systems to be able to operate at the same time, but independently of the other. The different wavelengths of light and different angles of scattering also allows the two optical smoke detection systems to identify characteristics of different stimulants within the detection zone 9.

The two optical smoke detection systems are arranged such that, in the presence of particulates such as smoke within the detection zone 9, light emitted by the light sources 5 and 7 is scattered by the particulates, and the scattered light is detected by the sensors 6 and 8. As the number of particulates within the detection zone 9 increase from zero, the amount of the light that is scattered increases, and the magnitude of the response signal from the sensors 6 and 8 increases. It is on the basis of the amount of scattered light detected by the sensors increasing above a threshold, and therefore the magnitude of the signals from the sensors increasing above a corresponding threshold, that the smoke detector is able to make a determination that a fire has been detected, although, as will be explained below, other things, such as the response of the proximity sensor and the ratio of the responses of the sensors 6, 8 are also used.

Figure 2:
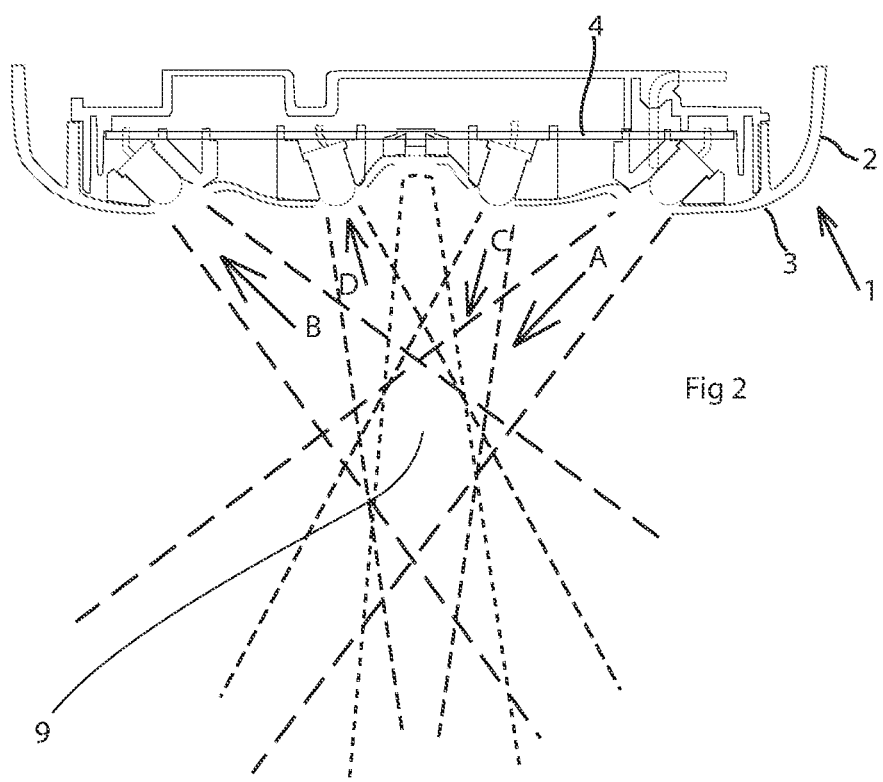
FIG. 2 is a schematic view of the chamberless smoke detector of FIG. 1 showing the path of light beams from light sources.

The operation of the optical smoke detection systems is shown more clearly in FIG. 2. The first light source 5 emits a first light beam 11 directed towards the detection zone 9, as indicated by arrow A. Any particulates within the detection zone 9 will cause scattering, and some of that scattered light will pass to the first sensor 6, as indicated by arrow B.

The second light source 7 emits a second light beam 12 directed towards the detection zone 9, as indicated by arrow C. Any particulates within the detection zone 9 will cause scattering, and some of that scattered light will pass to the second sensor 8, as indicated by arrow D.

The proximity detector 10 is an ultrasonic detector incorporating both an ultrasonic source and an ultrasonic sensor. The ultrasonic source emits an ultrasonic signal outwardly towards the detection zone 9, and if an object is present in the path of the ultrasonic signal, it will be reflected and that reflected ultrasonic signal will be received and detected by the ultrasonic sensor. The proximity detector will then generate a proximity signal indicting that an object has been detected. Of course, it will be realised that, because the proximity detector 10 relies on reflection of the ultrasonic signal, objects beyond the detection zone 9 will also be detected, and it is difficult to distinguish between objects within the detection zone 9 from those which are beyond the detection zone 9. However, since an object within the detection zone 9 would also cause some scattering of light in the optical smoke detection systems, the detector 1 is able to distinguish objects within the detection zone 9 from those which are outside of it by correlating the detection signal from the proximity detector 10 with the detection of scattering from one or both of the optical smoke detection systems.

As mentioned above, one of the advantages of operating two optical smoke detection systems at different wavelengths of light and at different scattering angles is that characteristics of any particulates within the detection zone 9 can be determined. As will be appreciated, different materials, when they burn, emit smoke particulates with different characteristics and with different constituents. Furthermore, non-smoke particulates, such as water droplets from steam, will have different characteristics from smoke particles. In particular, non-smoke particles can be identified from smoke particles. In this way, this embodiment is able to minimise false alarms caused by non-smoke particles entering the detection zone 9.

EXAMPLES

1. If an object passes beneath the detector 1 outside of the detection zone 9, this will be detected by the proximity detector, and the proximity detector will generate a proximity signal indicting that an object has been detected. However, the absence of scattered light detected by either of the optical smoke detection systems causes the detector 1 to determine that the detected object lies outside of the detection zone 9 and can be ignored.

2. If the object moves into the detection zone 9, the optical smoke detection systems will detect its presence. However, the proximity detector will also detect its presence, and the detector 1 is able to determine that an object has been detected and not smoke. In this situation, the scattering that the object causes in the two optical smoke detection systems will be about the same and so the response from the two sensors will also be about the same. If the two optical smoke detection systems were detecting smoke, the fact that they are detecting smoke using different wavelengths of light means that the magnitude of the responses from the two sensors would normally be very different from each other. An alarm condition is not triggered.

3. If steam or dust enter the detection zone 9 it will be detected by the optical smoke detection systems. In the absence of an object, the proximity detector does not generate a proximity signal indicting that an object has been detected. In this situation, the detector 1 determines that particulates have entered the detection zone 9. Because the two optical smoke detection systems operate at different wavelengths and at different angles, they are able to determine from the ratio of the response from the two sensors that the particulates are not smoke. An alarm condition is not signalled.

4. If smoke enters the detection zone 9, it will be detected by the optical smoke detection systems. In the absence of an object, the proximity detector does not generate a proximity signal indicting that an object has been detected. In this situation, the detector 1 determines that particulates have entered the detection zone 9. Because the two optical smoke detection systems operate at different wavelengths and at different angles, they are able to determine from the ratio of the response from two optical sensors that the particulates are smoke particulates. An alarm condition is signalled.

False alarms are minimised to a greater extent than is possible by the prior art device described above, and since a single detection zone 9 is used, the smoke detector 1 can be made to be smaller in size. Furthermore, arranging the light sources, the light sensors and the proximity detector in a line means that a smoke detector can be produced which is very narrow to facilitate installation in a greater range of locations.

In this embodiment, the ultrasonic proximity detector could be replaced by one which is optical or capacitive. Various other alternative arrangements of the smoke detector are also possible while remaining within the scope of the claimed invention.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A chamberless smoke detector, comprising:
   a first optical smoke detector having a first smoke detector light source arranged for emitting a first beam of light and a first scattered light sensor positioned to detect light from the first beam which is scattered by smoke present within a detection zone;
   a second optical smoke detector having a second smoke detector light source arranged for emitting a second beam of light and a second scattered light sensor positioned to detect light from the second beam which is scattered by smoke present within the detection zone; and
   an object proximity detector to detect an object in the detection zone,
   wherein the first smoke detector light source and the first scattered light sensor are inclined, with respect to a line normal to the chamberless smoke detector, by a greater angle than the second smoke detector light source and the second smoke sensor.

2. A chamberless smoke detector according to claim 1, wherein the proximity detector comprises a proximity signal source arranged for emitting a proximity signal beam towards the detection zone and a reflected proximity signal sensor arranged with the proximity signal source to detect a signal reflected from an object.

3. A chamberless smoke detector according to claim 2, wherein the proximity signal source is an ultrasonic signal source, and the proximity signal sensor is an ultrasonic signal sensor.

4. A chamberless smoke detector according to claim 1, wherein the first and second light sources are arranged to emit light of different frequencies.

5. A chamberless smoke detector according to claim 1, wherein the first light source, the first light sensor and the proximity sensor are arranged in a straight line across the chamberless smoke detector.

6. A chamberless smoke detector according to claim 1, wherein the first light source, the first light sensor, the second light source, the second light sensor and the proximity sensor are arranged in a straight line across the chamberless smoke detector.

7. A chamberless smoke detection method for a chamberless smoke detector, comprising:
   emitting a first beam of light with a first smoke detector light source and detecting the first beam of light with a first scattered light sensor positioned to detect light from the first beam which is scattered by smoke present within a chamberless detection zone;
   emitting a second beam of light with a second smoke detector light source and detecting the second beam of light with a second scattered light sensor positioned to detect light from the second beam which is scattered by smoke present within the detection zone; and detecting an object in the detection zone with an object proximity detector wherein the first smoke detector light source and the first scattered light sensor are inclined, with respect to a line normal to the chamberless smoke detector, by a greater angle than the second smoke detector light source and the second smoke sensor.

8. A method according to claim 7, further comprising the proximity detector emitting a proximity signal beam towards the detection zone and a reflected proximity signal sensor detecting the signal reflected from an object.

9. A method according to claim 8, wherein the proximity signal source is an ultrasonic signal source, and the proximity signal sensor is an ultrasonic signal sensor.

10. A method according to claim 7, wherein the first and second light sources are arranged to emit light of different frequencies.

11. A method according to claim 7, wherein the first light source, the first light sensor and the proximity sensor are arranged in a straight line across the chamberless smoke detector.

12. A method according to claim 7, wherein the first light source, the first light sensor, the second light source, the second light sensor and the proximity sensor are arranged in a straight line across the chamberless smoke detector.

* * * * *